United States Patent [19]

Jellicoe

[11] Patent Number: 5,047,032
[45] Date of Patent: Sep. 10, 1991

[54] METHOD AND APPARATUS FOR CUTTING JOINT SURFACES

[75] Inventor: Roger Jellicoe, Stafford, Australia

[73] Assignee: Richards Medical Company, Memphis, Tenn.

[21] Appl. No.: 260,259

[22] Filed: Oct. 20, 1988

[30] Foreign Application Priority Data

Oct. 21, 1987 [AU] Australia .................. PI 4991

[51] Int. Cl.$^5$ .............................................. A61B 17/56
[52] U.S. Cl. ........................................ 606/83; 606/79; 606/87; 606/88; 409/179
[58] Field of Search .......... 128/92 V, 92 VY, 92 VV, 128/92 VW, 92 VD, 92 Z, 305; 409/179; 606/79, 80, 83, 86, 87, 88, 89

[56] References Cited

U.S. PATENT DOCUMENTS

| | | | |
|---|---|---|---|
| 4,174,746 | 11/1979 | Walker et al. ................. | 409/179 X |
| 4,421,112 | 12/1983 | Mains et al. ................... | 128/305 X |
| 4,467,801 | 8/1984 | Whiteside ..................... | 128/92 VW X |
| 4,509,511 | 4/1985 | Neufeld ........................ | 128/92 VY X |
| 4,703,751 | 11/1987 | Pohl ............................... | 128/303 R X |
| 4,738,256 | 4/1988 | Freeman et al. .............. | 128/305 X |
| 4,787,383 | 11/1988 | Kenna ........................... | 128/303 R |
| 4,841,975 | 6/1989 | Woolson ........................ | 128/303 B X |

FOREIGN PATENT DOCUMENTS

| | | | |
|---|---|---|---|
| 1083013 | 6/1954 | France ........................... | 128/92 VJ |
| 250255 | 10/1987 | German Democratic Rep. ... | 128/92 VD |

*Primary Examiner*—Robert A. Hafer
*Assistant Examiner*—Kevin G. Rooney
*Attorney, Agent, or Firm*—Pravel, Gambrell, Hewitt, Kimball & Krieger

[57] ABSTRACT

Surgical instrumentation and a method for cutting bones on one or both sides of a joint such as the knee joint to allow the application of a joint prosthesis. A rod is inserted into the medullary canal of the bone to be cut. The rod is secured within the medullary canal and a router guide is mounted on the rod for rotation thereabout while being restrained against movement axially of the rod. A router or side cutting drill is inserted through the router guide into contact with the rod and actuated to rotate about its own axis. The router guide and the router are then caused to rotate about the rod to thereby cut the bone to produce a substantially planar surface thereon suitable to bear against a joint prosthesis.

7 Claims, 4 Drawing Sheets

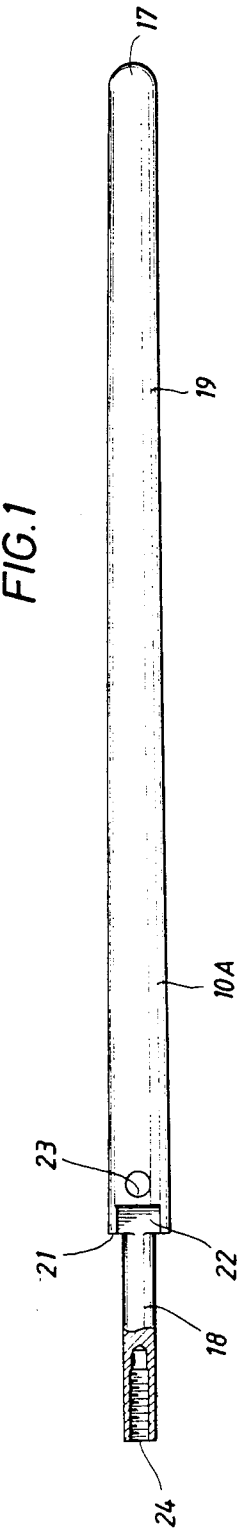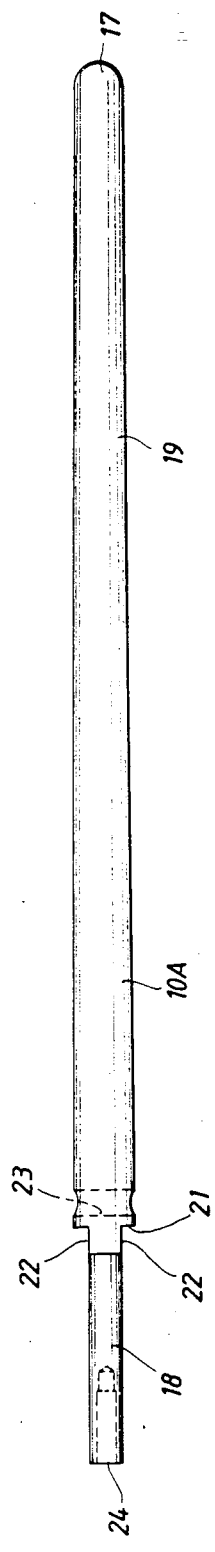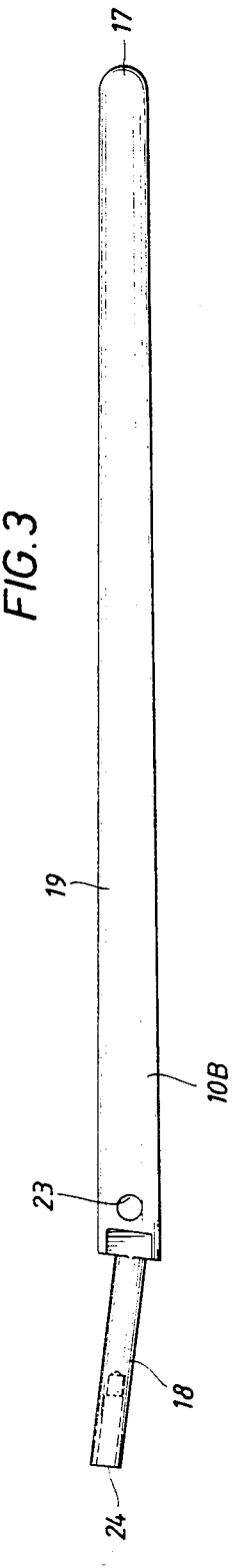

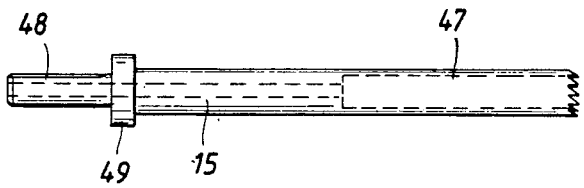
FIG. 7
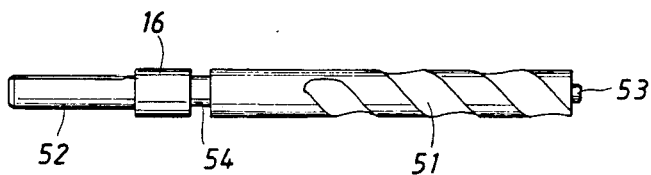
FIG. 8
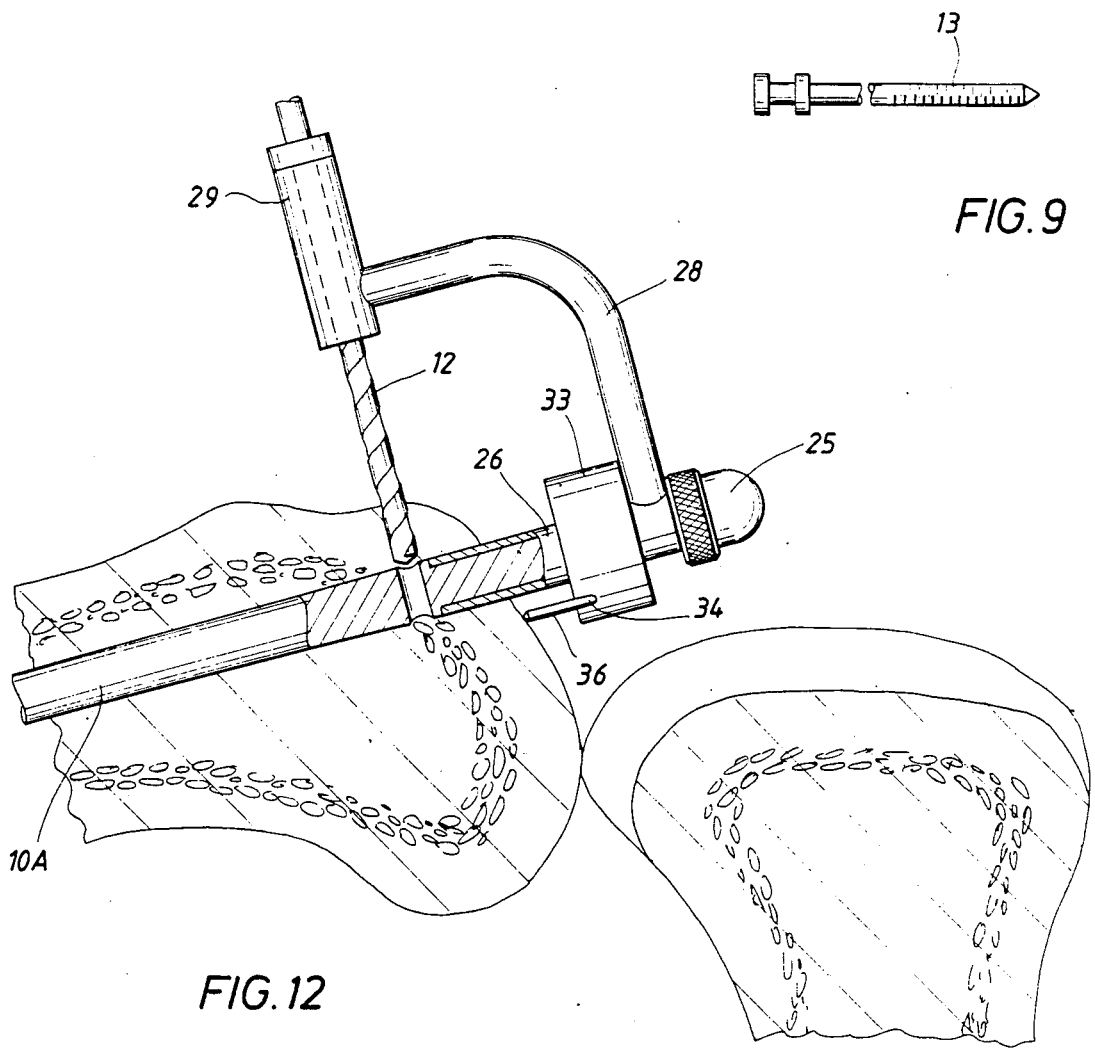
FIG. 9
FIG. 12

METHOD AND APPARATUS FOR CUTTING JOINT SURFACES

TECHNICAL FIELD OF THE INVENTION

The present invention relates to surgical instrumentation for use in cutting bones adjacent joints, and to a method for conducting such surgery. The instrumentation and method of the present invention are of particular application in total knee arthroplasty.

BACKGROUND ART

In carrying out total knee arthroplasty it is necessary to cut both the distal femoral and proximal tibial bones to remove the surface of articulation therefrom. Such surgery is commonly required in degenerative bone disease of the joints or in chronic arthritis.

The major difficulty encountered with instrumentation presently available, and in the presently used methods, is that it is often very difficult to obtain precise flat bone cuts. For optimum functional performance and long term results cementable or cementless total knee replacement components demand precise flat bone cuts resulting in an even distribution of load at implant/bone interface. Almost all prior art systems provide for cuts to be made with a narrow oscillating saw blade over or through a metal jig. The flexibility of the blade allows the saw to deviate, often taking the path of least resistance when passing through sclerotic bone and resulting in inaccurate cuts or uneven surfaces.

DISCLOSURE OF THE INVENTION

It is an object of the present invention to provide instrumentation and a method by which substantially flat even cuts may be made, transversely to the long axis of the bone on either side of the joint.

In a first aspect the present invention is directed to surgical instrumentation for use in cutting bones on one or both sides of a joint, which includes a rod adapted for insertion into the medullary canal of a bone to be cut, means for locking the rod into a desired position within the bone to be cut, and guide means for positioning a bone cutting implement in a desired position relative to the bone, the guide means being adapted for connection to the rod in a manner such that the guide means is free to rotate about the long axis of the rod, but unable to move along said axis.

In a preferred embodiment of the present invention the bone cutting implement consists of a rigid router or side cutting twist drill. In use, prior to the cutting of the bone with the rigid router a hollow mill is inserted through the guide means, and a hole bored in the bone, prior to the insertion of the rigid router.

In a second aspect the present invention is directed to a method of cutting the bone on one or both sides of a joint in which the following steps are used:
1. Inserting a rod into the medullary canal of the bone to be cut;
2. Locking the rod in the required position within the bone to be cut;
3. Mounting a guide means on the rod in a manner such that the guide means is free to rotate about the long axis of the rod, but unable to move along said axis;
4. Inserting a bone cutting implement through the guide means; and
5. Actuating the bone cutting implement and rotating the guide means about the long axis of the rod such that a substantially planar cut is produced in the bone transversely to the long axis of the rod.

In a preferred embodiment of this aspect of the present invention, the bone cutting implement includes a rigid router or side cutting twist drill. In this embodiment a hollow mill is inserted into the guide means and a hole bored in the bone or other tissue between the guide means and the rod. Subsequently, the rigid router is inserted through the guide means into this hole in the bone. Upon actuation, the bone is cut in an arc lying in a plane transversely of the long axis of the rod as the guide means is rotated about the rod.

BRIEF DESCRIPTION OF THE DRAWINGS

In order that the nature of the present invention may be more clearly understood a preferred form thereof will now be described with reference to the following drawings, in which:

FIG. 1 is a side elevational view of a rod for insertion into the medullary canal of a human tibia for use as part of the surgical instrumentation according to the present invention;

FIG. 2 is a further side elevational view of the rod of FIG. 1;

FIG. 3 is a side elevational view similar to FIG. 1 of a rod for use as part of the surgical instrumentation according to the present invention but for insertion into the medullary canal of a human femur;

FIG. 7 is a side elevational view of a hollow mill for use in the router guide of FIG. 6;

FIG. 8 is a side elevational view of a router or side cutting drill for use in the router guide of FIG. 6;

FIG. 9 is a side elevational view of a locking nail for use as part of surgical instrumentation according to the present invention;

FIG. 12 is a longitudinal sectional view through the human knee joint of FIG. 9 showing part of the surgical instrumentation being used to form a hole to receive a locking nail to retain the rod in position in the medullary canal of the patient's tibia.

DETAILED DESCRIPTION OF A PREFERRED EMBODIMENT

Figure 4:
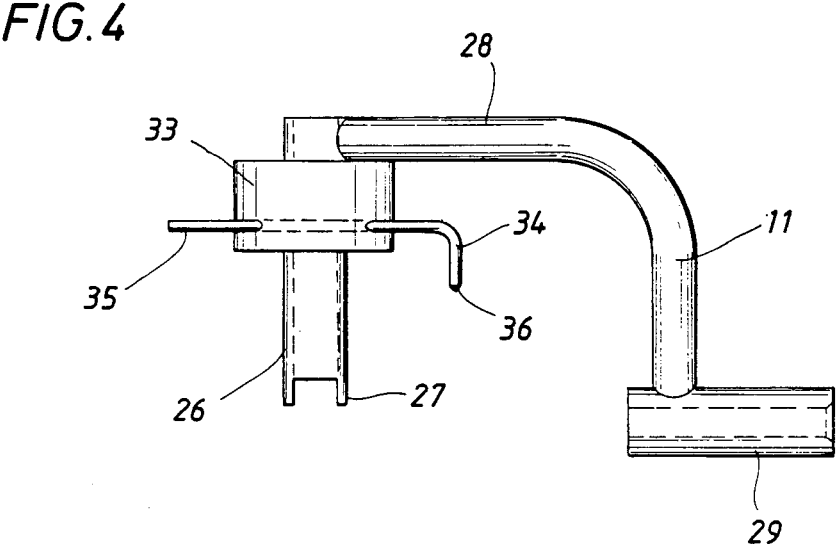
FIG. 4 is a side elevational view of a locking nail drill guide for use as part of the surgical instrumentation according to the present invention to which is attached a depth guide adapted for use when the instrumentation is used on a human tibia.
Figure 5:
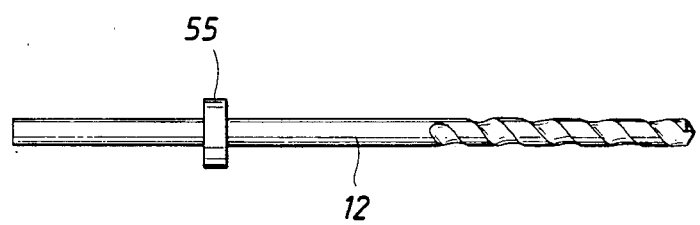
FIG. 5 is a side elevational view of a twist drill with depth stop for use in the drill guide shown in FIG. 4.
Figure 6:
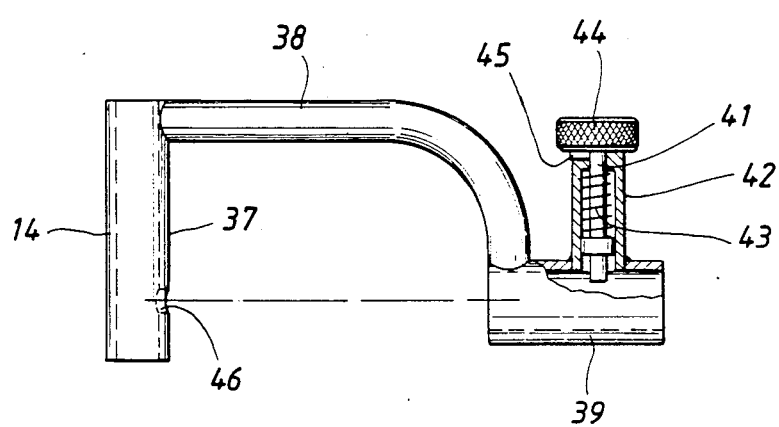
FIG. 6 is a partly cut away side elevational view of a router guide with locking mechanism for use as part of the surgical instrumentation according to the present invention.

The surgical instrumentation according to the preferred embodiment of the invention adapted for use in a total knee arthroplasty comprises an intramedullary rod 10, a locking nail drill guide 11, a drill 12, locking nails 13, a router guide 14, a hollow mill 15, and a router or side cutting drill 16.

Figure 11:
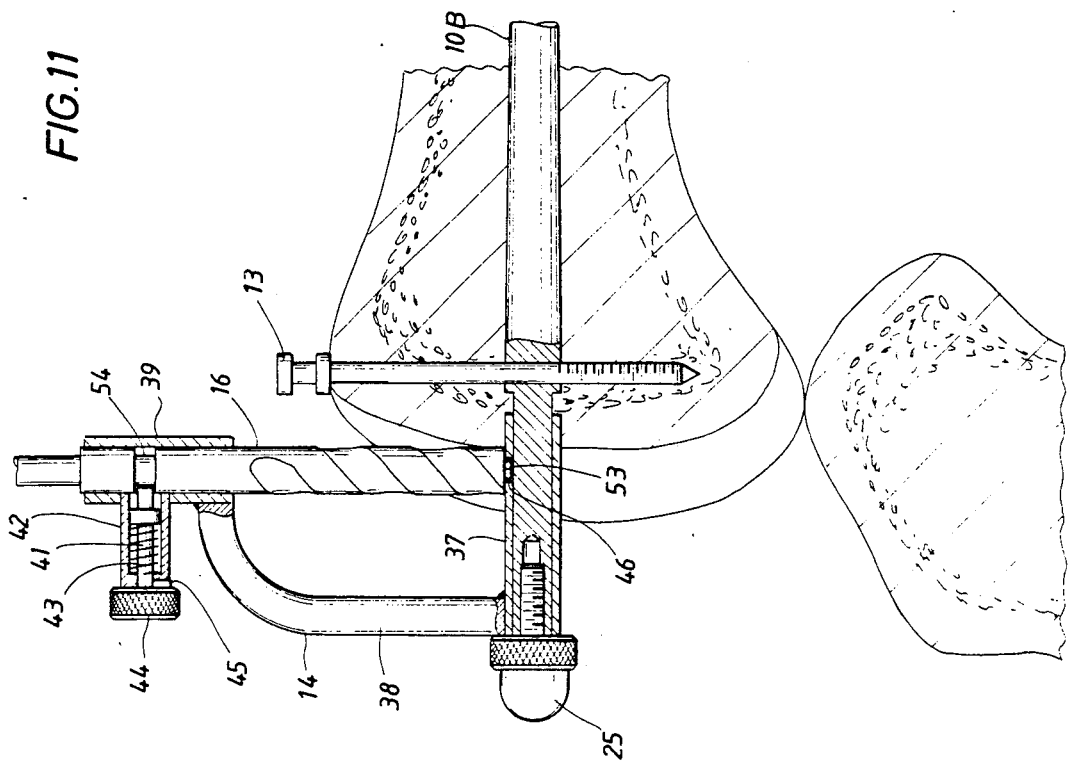
FIG. 11 is a longitudinal sectional view through the human knee joint of FIG. 9 showing the router guide and router in position on the rod secured in the medullary canal.
Figure 10:
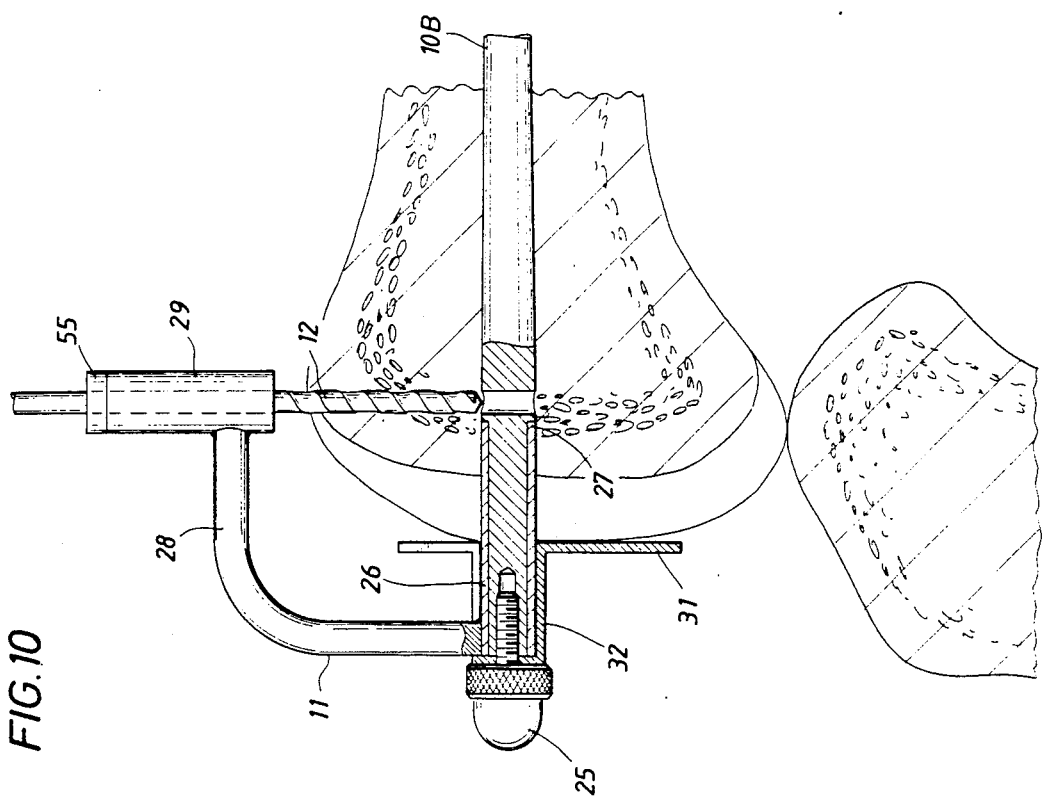
FIG. 10 is a longitudinal sectional view through a human knee joint showing part of the surgical instrumentation being used to form a hole to receive a locking nail to retain the rod in position in the medullary canal of the patient's femur.

The intramedullary rod 10A shown in FIGS. 1 and 2 is adapted for insertion into the human tibial medullary canal and comprises an elongate shaft 19 having at one end a full spherical radius 17 and at the other end a cylindrical portion 18 of the reduced diameter. The portion 18 and the shaft 19 are in axial alignment and join at a shoulder 21. The juncture of shaft 19 and cylindrical portion 18 is formed with a pair of diametrically opposed fats 22. The shaft 19 tapers inwardly slightly along its length from the shoulder 21 to the fully radiused end 17. A diametrically aligned hole 23 extends through the shaft 19 at right angles to flats 22 adjacent shoulder 21. The free end of the portion 18 is formed with a threaded axially extending hole 24 adapted to receive a locking bolt 25 (see FIGS. 10, 11 and 12.)

An intramedullary rod 10B for use in the human femoral medullary canal is shown in FIG. 3 and is identical with rod 10A shown in FIGS. 1 and 2 with the exception that the axes of the cylindrical portion 18 and the shaft 19 are offset by 7° to compensate for the fact that the articular surfaces of the human femur are offset from its axis by approximately that amount due to the femur angling in from the hips to the knee. It will be recognized by persons skilled in the art that in some cases the angle between the axes of the shaft 19 and the cylindrical portion 18 may be varied from the 7° angle described to suit a particular patient. It will be appreciated that the same rod 10B may be used for both the right and left legs by rotation about its long axis through 180°. The shaft 19 is a right cylinder rather than tapering due to the greater size of the medullary canal.

The drill guide 11 includes a tubular body 26 adapted to be a close sliding fit on the portion 18 of the rod 19. The body 26 is formed at one end with a pair of projections 27 adapted to engage with the flats 22 of the rod 10 and prevent relative rotation therebetween when the drill guide 11 is assembled on the rod 10. An arm 28 extends radially from the other end of body 26 and then is bent through 90° to extend parallel to body 26. At its free end arm 28 is carried a tubular guide member 29. The guide member 29 is so positioned to guide the drill 12 through the hole 23 in the rod 10 in use.

The drill guide 11 is adapted for use with a depth guide which limits the extent to which the rod 10 may be inserted into the medullary canal and thus the amount of bone cut from the articular surface to be replaced. In the case of a femur the guide means may comprise a plate 31 (as seen if FIG. 10) having a recess 32 adapted to fit about the body 26 of the drill guide 11 and be retained thereon by bolt 25. The plate 31 is, in use, adapted to bear against one or both of the femoral condyles and ensure that a fixed amount of bone is removed from the femur in all cases.

In the case of the tibia it may be desirable to remove the minimum amount of bone and for this reason a different type of depth guide is used. In this case the depth guide comprises a collar 33 (see FIGS. 4 and 12) rotatably mounted on the outside of the body 26 of the drill guide 11 and adapted to bear against the arm 28. The collar 33 carries an L-shaped stylus 34. The stylus 34 has a long arm 35 slidably disposed in a bore in the collar 33 normal to the axis thereof. A short arm 36 of the stylus 34 has a pointed tip adapted to be abutted against the lowest point on the tibial articular surfaces. The instrumentation is then adapted to cut the bone to the tibia down to a plane a fixed distance beyond the low point abutted by the stylus 34.

The router guide 14 comprises a tubular body 37 adapted to be a close sliding fit on the portion 18 of the rod 10 and to be rotatable thereabout. An arm 38 extends radially from one end of the body 37 and is bent through 90° to extend parallel to body 37. At this free end the arm 38 carries a tubular guide member 39. The tubular guide carries a radially arranged locking pin 41 which is mounted in a radially arranged tubular housing 42. A spring 43 in the housing and surrounding the pin 41 urges the free end of pin 41 radially inwardly into the bore of the tubular guide member 39. The pin 41 includes at its outer end a knurled knob 44 adapted to abut against the radially outer end of the housing 42. The underside of the knob 44 is formed with a boss 45 adapted to be normally received in a recess in the end of housing 42. If it is desired to maintain the free end of the pin 41 retracted from the bore of the tubular guide member 39 the pin 41 may be pulled radially outwardly and rotated such that boss 45 bears against the outer end of housing 42. The body 37 of the router guide 14 is formed with a radial hole 46 in axial alignment with the bore of the tubular guide member 39.

The hollow mill 15 includes a tubular body 47 having an array of cutting teeth around its free end. The body 47 axially abuts with a stem 48 adapted to be gripped by the chuck of a conventional orthopaedic drill. A stop collar 49 is formed on the mill 15 intermediate its ends. For cleaning purposes the mill 15 is fully canulated.

The router of side cutting drill 16 includes in axial alignment a stem 52, a cutting body 51 and a projection 53. The stem 52 includes a circumferential groove 54.

In use the knee joint is exposed in the normal way with the leg held in flexion. A twist drill, normally ⅜ diameter, is used to drill through the distal femoral cortical surface in the intra condylar notch region and in line with the medullary canal. This drill hole allows insertion of the rod 10B into the femoral medullary canal.

The rod 10B is assembled with the depth guide 31 and the locking nail drill guide 11 on the portion 18 of the rod 10B and held in place by the bolt 25. The rod 10B is then inserted into the femoral medullary canal and is rotated until the axis of the guide member 29 is at 90° to the anterior portion of the distal femur and the depth guide plate 31 parallel to the posterior aspect of the femoral condyles and with the angled offset appropriate for either the right or left leg as the case may be. If desired, a nail 13 may be inserted through a hole (not shown) in the depth guide plate 31 into the distal end of the femur to retain the drill guide 11 in the correct orientation relative to the femur.

The drill 12 is then introduced through the guide member 29 and caused to rotate using a conventional orthopaedic drill. The drill 12 is then caused to drill through the femur until a stop collar 55 on the drill 12 abuts against the guide member 29. The drill 12 is then removed and a short nail 13 introduced into the hole so formed to temporarily retain the rod 10B in place in the bone. The depth guide 31 and the drill guide 11 may then be removed from the rod 10B and the short nail replaced by a longer such nail 13 which will extend through the hole 23 in the rod 10B and into the cancellous bone on the other side of the rod 10B.

The router guide 14 may then be positioned on the portion 18 of the rod 10B and rotatably retained thereon by bolt 25. The hollow mill 15 is then introduced through guide member 39 with the pin 41 withdrawn. The mill 15 is caused to rotate using a conventional orthopaedic drill and is driven through the bone or other tissue between the guide member 39 and the body member 37 of the router guide 14. After withdrawal of the mill 15 the router 16 is positioned in the guide member 39 with the projection 53 extending into the hole 46 in the body 37 of router guide 14 and the pin 41 extending into the groove 54 in the router 16. The router 16 is then caused to rotate about its axis using a conventional orthopaedic drill. The router guide 14 is then caused to rotate as far as it can in either direction about the portion 18 of the rod 10. The router 16 cuts into and then through the bone on either side of the intra condylar notch. When the maximum possible arc of the cut has been made the whole of the surgical instrumention is removed from the femur and the cut completed using an oscillating saw.

The procedure for resecting the tibia is similar to that for the femur with the exception that after the hole has been drilled through the proximal tibial cortical surface in line with the medullary canal it normally will be necessary to slightly enlarge the medullary canal with a reamer to accept the rod 10A. This enlargement is preferably carried out with a blunt ended reamer (not shown) having the shape of the rod 10A having longitudinally extending cutting blades along its sides. Such a reamer will ensure that the medullary canal is enlarged just enough to receive the rod 10A without lateral movement while not being likely to pierce the bone surrounding the canal.

The drill guide 11 is assembled with the depth guide 33. The stylus 34 is moved radially of the axis of rod 10 and rotated about it until the tip of the stylus 34 is in contact with the lowest point of the upper tibial surface. If desired styli of different lengths may be used or there may be a plurality of holes in the collar 33 through which the stylus 34 may be slid to allow the resection of the tibia to be effected at different distances below the level identified by the tip of the stylus. It is also possible to use the depth guide to establish the highest point on the tibia and to use that as a reference point from which to establish the cutting depth. The resection is then completed as described above.

The surfaces so formed on the femur and the tibia have been found to be substantially flat and well adapted to receive a total knee prosthesis subject to he making of such other cuts as are conventionally required to fit such a prosthesis.

The foregoing disclosure and description of the invention are illustrative and explanatory thereof, and various changes in the size, shape and materials, as well as in the details of the illustrated construction may be made without departing from the spirit of the invention.

I claim:

1. Surgical instrumentation for use in cutting bones to a pre-determined depth on one or both sides of a joint, comprising:
   (a) a rod adapted for insertion into, and rigid positioning within, the medullary canal of the bone to be cut;
   (b) a depth limiting means to control the extent to which the rod may be inserted into the medullary canal of the bone to be cut;
   (c) a first guide frame means adapted for connection to the rod and including a hole extending diametrically therethrough for guiding a drill to form a hole transversely of the bone to be cut;
   (d) a locking means including an elongated member adapted to extend through the hole in the bone and through a hole in the rod for locking the rod into a desired position within the bone;
   (e) a second guide frame means for positioning and guiding a bone cutting or drilling implement in a desired position relative to the bone;
   (f) the rod including a proximal end capable of sequentially and removably receiving the first and second guide frame means;
   (g) a guide frame rotational locking means capable of holding the first and second guide frame means against rotation relative to the rod at a fixed axial location;
   (h) a guide frame axial locking means capable of allowing the second guide frame means to rotate relative to the rod at a fixed axial location; and
   (i) means for connecting the first and second guide frame means to the proximal end of the rod.

2. Surgical instrumentation as claimed in claim 1 in which the depth limiting means comprises a plate adapted to be connected to one end of the rod.

3. Surgical instrumentation as claimed in claim 1 in which the depth limiting means comprises a stylus rotatably mounted on the rod and adapted to be moved radially relative thereto.

4. Surgical instrumentation as claimed in claim 1 in which the second guide frame means includes a tubular body adapted to closely surround an end portion of the rod and to rotate thereabout while being restrained against movement axially of the rod.

5. Surgical instrumentation as claimed in claim 1 in which the bone cutting implement comprises a router or side cutting drill adapted to extend radially of the rod and to be rotated about its own longitudinal axis.

6. A method of cutting, to a predetermined depth, the bone on one or both sides of a joint comprising the steps of:
   (1) Inserting a rod into the medullary canal of the bone to be out;
   (2) Locking the rod in the required position within the bone to be cut;
   (3) Mounting a guide means on the rod in a manner such that the guide means is free to rotate about the long axis of the rod, but unable to move along said axis;
   (4) Mounting a bone cutting implement on the guide means; and
   (5) Actuating the bone cutting implement and rotating the guide means about the long axis of the rod such that a substantially planar cut is produced in the bone transversely to the long axis of the rod.

7. A method as claimed in claim 6 in which the comprises a knee joint of a human.

* * * * *